（12）United States Patent
Schur et al.

(10) Patent No.: US 7,455,675 B2
(45) Date of Patent: Nov. 25, 2008

(54) DEVICE AND METHOD FOR WITHDRAWING A TUBULAR BODY PART

(75) Inventors: Israel Schur, Englewood, NJ (US); William M. Appling, Granville, NY (US)

(73) Assignee: AngioDynamics, Inc., Queensbury, NY (US)

( * ) Notice: Subject to any disclaimer, the term of this patent is extended or adjusted under 35 U.S.C. 154(b) by 0 days.

(21) Appl. No.: 10/458,783

(22) Filed: Jun. 10, 2003

(65) Prior Publication Data

US 2004/0087967 A1 May 6, 2004

Related U.S. Application Data

(60) Provisional application No. 60/470,077, filed on May 13, 2003, provisional application No. 60/424,528, filed on Nov. 6, 2002.

(51) Int. Cl.
*A61B 17/00* (2006.01)
(52) U.S. Cl. ....................................................... 606/139

(58) Field of Classification Search .......... 606/181–185, 606/139, 142, 144, 148, 213, 214; 600/564, 600/566, 567
See application file for complete search history.

(56) References Cited

U.S. PATENT DOCUMENTS

| 5,758,665 | A |   | 6/1998 | Suval |
|---|---|---|---|---|
| 5,792,168 | A |   | 8/1998 | Suval |
| 5,928,250 | A | * | 7/1999 | Koike et al. ................. 606/139 |
| 6,071,292 | A | * | 6/2000 | Makower et al. ............ 606/158 |

* cited by examiner

*Primary Examiner*—Kevin T Truong
(74) *Attorney, Agent, or Firm*—Abelman Frayne & Schwab; Harry K. Ahn

(57) ABSTRACT

A device for withdrawing a tubular body part such as a varicose vein is provided. A needle is inserted through a skin. The needle contains therein an engaging element in an undeployed state. After the needle is inserted, the engaging element is pushed out of the needle and is typically deployed inside the vein. The vein is now ready to be withdrawn by the deployed engaging element. Using a puncture device that also contains a deployable engaging element allows the puncture site to be small and causes less trauma to the surrounding tissue.

10 Claims, 14 Drawing Sheets

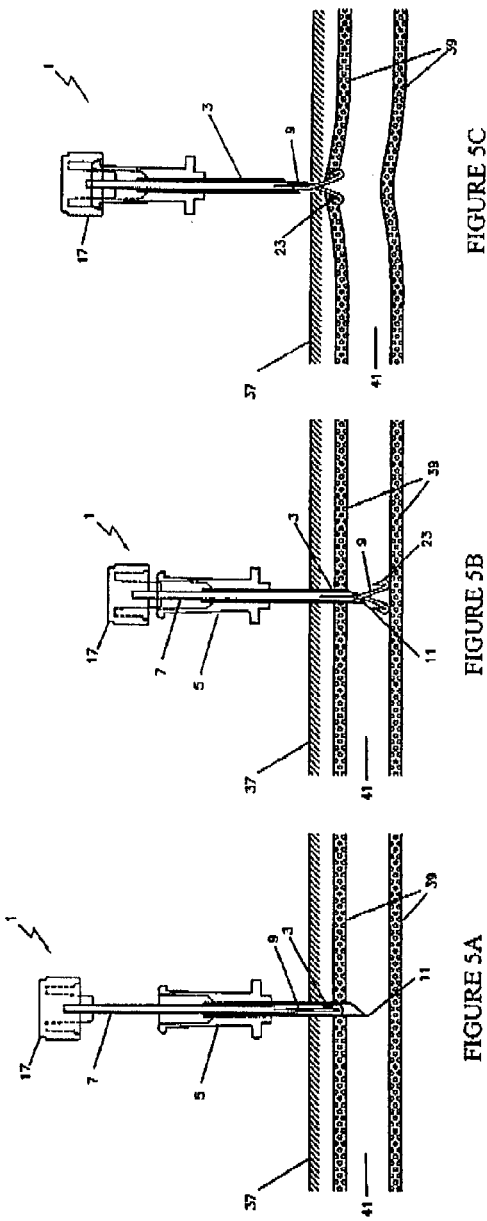
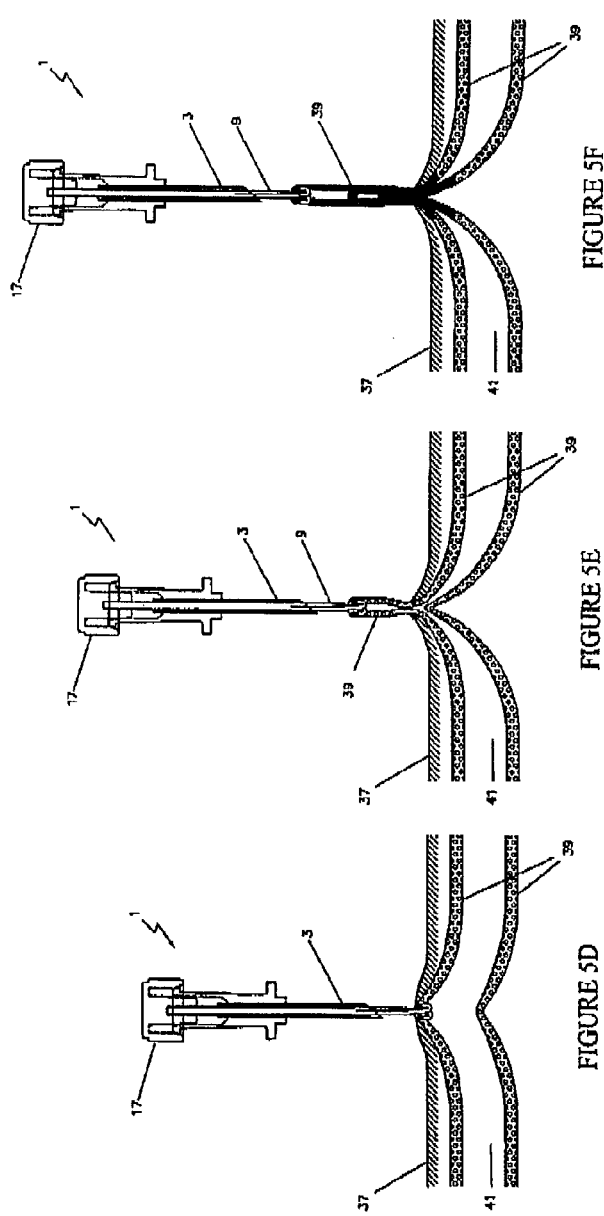

DEVICE AND METHOD FOR WITHDRAWING A TUBULAR BODY PART

CROSS-REFERENCE TO RELATED APPLICATIONS

This application claims priority to U.S. provisional application No. 60/424,528, filed Nov. 6, 2002 and U.S. provisional application No. 60/470,077, filed May 13, 2003, both of which are incorporated into the present specification by reference.

FIELD OF THE INVENTION

The present invention relates to a medical device for withdrawing a tubular body part, and more particularly, to a device and method for the treatment of varicose veins using ambulatory phlebectomy techniques.

BACKGROUND OF THE INVENTION

Varicose veins of the lower extremities is one of the most common medical conditions of the adult population. It is estimated that varicose veins affect approximately 25% of adult females and 10% of males. Symptoms include discomfort, aching of the legs, itching, cosmetic deformities, and swelling. If left untreated, varicose veins may cause medical complications such as bleeding, phlebitis, ulcerations, thrombi and lipodermatosclerosis.

Unlike arteries, veins are thin-walled and contain valves that control blood flow. The valves act as one-way flaps that open to allow blood to flow into the deeper veins and close to prevent backflow into the superficial veins. Varicose veins are caused when those valves become incompetent and can no longer prevent the reflux of blood into the superficial veins. Venous pressure builds at the site of the incompetence due to backflow and "pileup" of blood. Because the veins are thin walled and not able to withstand the increased pressure, the veins become dilated, tortuous and engorged.

Traditional treatments for varicosities include both temporary and permanent techniques. Temporary treatments involve use of compression stockings and elevation of the diseased extremities. While providing temporary relief of symptoms, these techniques do not treat the incompetent valves that are the underlying cause of the varicose veins.

Permanent treatments include surgical excision of the diseased segments and occlusion of the vein through chemical or thermal means. These treatment types focus on the elimination of underlying incompetent vein reflux by either removal or occlusion of the veins. Although permanent treatments focus on elimination of reflux, there are drawbacks and complications associated with surgical removal and vein occlusion procedures.

Surgical excision often requires general anesthesia and a long recovery period. Even with its clinical effectiveness, surgical excision is rapidly becoming an outmoded procedure due to the high costs of treatment and risk of complications from surgery. In addition, the cosmetic results are often unsatisfactory due to scarring.

A new thermal treatment option that was recently developed to replace the surgical treatment procedure utilizes thermal energy from either radio frequency (RF) or laser light. The thermal energy from the RF signal or laser is applied to the inner wall of the diseased vein. In reaction to the thermal energy, the vein becomes occluded. Reported recurrence rates are low with relatively fast recovery times. The thermal procedure is done on an outpatient basis with the use of local anesthesia. Although complications are usually minor, in some rare cases, serious dermal burns, focal numbness, vessel perforations and pulmonary emboli have been reported. However, drawbacks of the thermal treatment of varicose veins include the high cost of equipment for the generator and disposables as well as the inability to treat all vein sizes. In addition, the size of the thermal delivery system limits the size of veins that can be treated with this method.

Chemical occlusion, also known as sclerotherapy, is an in-office procedure involving the injection of an irritant chemical into the vein. The chemical acts upon the inner lining of the vein walls causing vessel fibrosis and occlusion of blood flow. Although the chemical occlusion procedure is a popular treatment option, complications can be severe including skin ulceration, anaphylactic reactions and permanent skin staining. Treatment is also limited to veins of a particular size range, typically smaller veins. Other drawbacks include a relatively high recurrence rate due to vessel re-canalization and inability to treat the underlying valve incompetence originating at the saphenous-femoral junction.

The incompetent feeding vein may be deep and angled relative to the skin surface such that it is not visible or palpable. The source of reflux in these deep or non-visible veins often must be eliminated as part of the overall treatment procedure. Traditionally, either ultrasound-guided sclerotherapy or stab avulsion techniques have been used to eliminate the reflux in these deeper veins. As previously described, ultrasound-guided sclerotherapy is often not completely effective in eliminating the reflux source and as a result the treatment may need to be repeated. With stab avulsion, an incision up to 4 to 5 mm long is first made in the skin. Hemostatic forceps or another similar tool is then inserted into the incision and the vein segment is pulled up through the incision. The disadvantage of this technique is the size of the incision which causes unnecessary trauma and unsightly scarring.

In contrast to the above procedures, ambulatory phlebectomy has become a widely accepted medical technique in the treatment of varicose veins, particularly tributaries. Ambulatory phlebectomy is generally used to remove varicosities of the tributary veins that are caused either by greater-saphenous vein reflux or by isolated weakness of the vessel walls without underlying valve incompetency. When greater saphenous vein reflux is the cause of the varicosities, elimination of the reflux source is first performed using thermal, surgical or chemical treatment as described above. Ambulatory phlebectomy is then used as an adjunctive procedure to treat the tributary veins. When varicose tributaries are not directly connected to an incompetent larger vein, ambulatory phlebectomy can be used as the primary treatment procedure.

The ambulatory phlebectomy technique for tributary varicosities involves extraction of the varicose vein segment using small incisions through the skin. Ambulatory phlebectomy has several advantages over more traditional treatment techniques. As a minimally invasive procedure, ambulatory phlebectomy is performed in an outpatient setting using local anesthesia. The small size of the incisions, typically 1 to 2 mm, eliminates the need for skin suturing, improves cosmetic appearance and reduces recovery time. Risk of thromboembolic events and other serious complications are minimal with this technique. In addition, ambulatory phlebectomy can be used to successfully treat tributary varicose veins of almost any size and at almost any anatomical site as long as they are visible and palpable.

One main disadvantage of ambulatory phlebectomy as a varicose vein treatment is the relatively long procedure time. Specifically, the varicose vein is first mapped out on the skin surface. Local or tumescent anesthesia is then injected along the length of the treatment zone. After the injection of anesthesia, the skin is incised using a scalpel or needle. To capture and extract the vein, the scalpel is removed and a surgical hook-like instrument is inserted and positioned under the vein. The vein is grasped and withdrawn. Thus, ambulatory phlebectomy is essentially a blind procedure in which the physician does not know that the correct target vein has been hooked until it is withdrawn through the incision and can be seen. This blind procedure results in inadvertent hooking of other bodily structures such as nerves and can also result in incomplete vein segments being extracted. Often, several attempts at pulling, rotating and twisting the hook tool is required before the vein is successfully engaged. These movements can cause trauma to the surrounding tissue and significant post-procedural bruising.

The use of surgical hooks, forceps and toothed clamps to retrieve varicose vein segments is well known in the art. Perhaps the most well known of these devices is the Muller phlebectomy hooks, which were first introduced to the market in the 1970s. Typically, the hook is inserted into a previously created incision. The hook is rotated to grasp the vein and then pulled out of the incision. Thus, the Muller design required two separate surgical instruments to perform ambulatory phlebectomy: a scalpel for forming the incision; and a hook for engaging and retrieving the vein.

A supposed improvement on the Muller technique was disclosed by Suval in U.S. Pat. Nos. 5,792,168 and 5,758,665, both of which are incorporated herein by reference. Suval discloses a trigger-activated surgical device for varicose vein removal in the '168 patent. A solid needle at the end of an elongated shaft is positioned adjacent to the vein. When the trigger is depressed, the vein is gripped from the outside between the distal end of the barrel and the flat proximal surface of the needle. In the '665 patent, Suval teaches a method for engaging and removing a vein using a single surgical instrument that is placed adjacent to the vein.

While Suval teaches a design for engaging and removing the vein by using a single instrument, the technique still suffers from the same drawbacks that are present in any ambulatory phlebectomy. Because the device is positioned adjacent to the vein rather than within the vein, there is no visual confirmation that the engaged structure is actually a vein until it is brought to the skin surface. Thus, the phlebectomy procedure using Suval's device and method remains a blind procedure with the inherent risks of inadvertently extracting a nerve or other non-targeted structure. As with traditional phlebectomy hooks, Suval's device may need to be rotated, pulled, twisted and otherwise maneuvered to successfully capture the vein for extraction. Since Suval's device cannot precisely target the vein, repeated attempts may be required before the vein is successfully hooked and extracted resulting in extended procedural time.

Perhaps the most serious drawback of ambulatory phlebectomy including the Suval procedure is the risk of inadvertently hooking nerves or other body tissue. Because nerves and veins are often located in close proximity to each other and often have the same appearance, it is difficult to distinguish a nerve either tactilely or visually when using a traditional phlebectomy hook. As a result, a nerve may be mistakenly hooked and withdrawn during an ambulatory phlebectomy procedure, resulting in temporary or even permanent nerve damage to the patient. Suval's teaching does not include any mechanism for identifying the correct positioning prior to removal from the incision.

Therefore, it is desirable to provide an improved device and method for use in ambulatory phlebectomy that eliminates the need for a phlebectomy hook, reduces procedure time, reduces cosmetic imperfections and provides the capability to check for correct positioning prior to removal of the target vein.

SUMMARY OF THE DISCLOSURE

According to the principles of the present invention, a device for withdrawing a tubular body part such as a varicose vein is provided. The device includes a needle that is inserted through a skin. The needle contains therein an engaging element in an undeployed state. Once the needle is inserted, the engaging element is pushed out of the needle and is typically deployed inside the vein. The vein is now ready to be withdrawn by the deployed engaging element.

By using a puncture device that also contains a deployable engaging element, the present invention allows the puncture site to be small and causes less trauma to the surrounding tissue.

BRIEF DESCRIPTION OF THE DRAWINGS

FIGS. 5A-5F depict a method of insertion and withdrawal of the targeted phlebectomy device of FIG. 1.

DETAILED DESCRIPTION OF THE INVENTION

Figure 1:
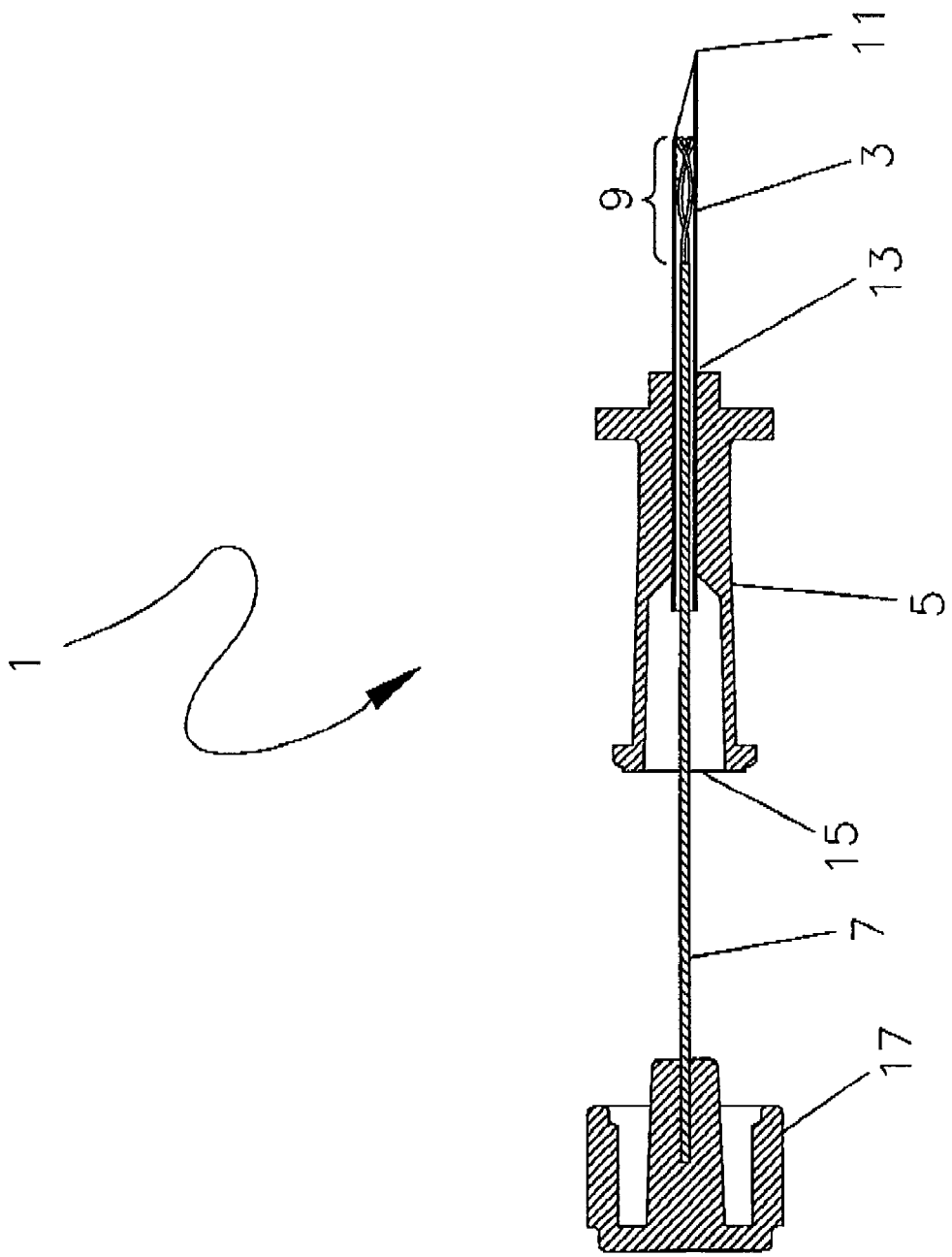
FIG. 1 is a cross-sectional view of a preferred embodiment of the targeted phlebectomy device having an engaging element in an undeployed position.

A preferred embodiment of the targeted phlebectomy device 1 is shown in FIG. 1. The assembly includes a needle 3, a hub 5, a deployment device such as a plunger rod 7 and an engaging element 9. In the embodiment shown, the needle 3 is a medical grade stainless-steel needle cannula with a sharp, beveled tip 11 at the distal portion of the needle 3. The proximal section of needle 3 extends into and is secured to a through lumen at opening 13 of the hub 5. A standard adhesive or other bonding method can be used to securely attach the needle 3 to the through lumen opening 13. The needle 3 typically extends distally beyond the through lumen opening 13 by approximately 2.5 cm, although various needle 3 cannula lengths can be used.

Housed within the lumen of the needle 3 is the deployable engaging element 9. The engaging element 9 is attached to the distal section of the plunger rod 7 through either a welding or bonding process, as is well known in the art. The weld section of the plunger rod 7 and the engaging element 9 is depicted as in FIG. 2 as 19. At its proximal end, the plunger rod 7 may be attached to a deployment device stop such as a standard luer end cap 17 or other terminating fitting. The plunger rod 7 is slidably coupled to the needle 3 and can be moved longitudinally through the hub 5 and needle 3 lumens by applying pressure to the end cap 17. Typically, the plunger rod 7 is made of medical grade stainless steel, although other materials can be used.

Figure 2:
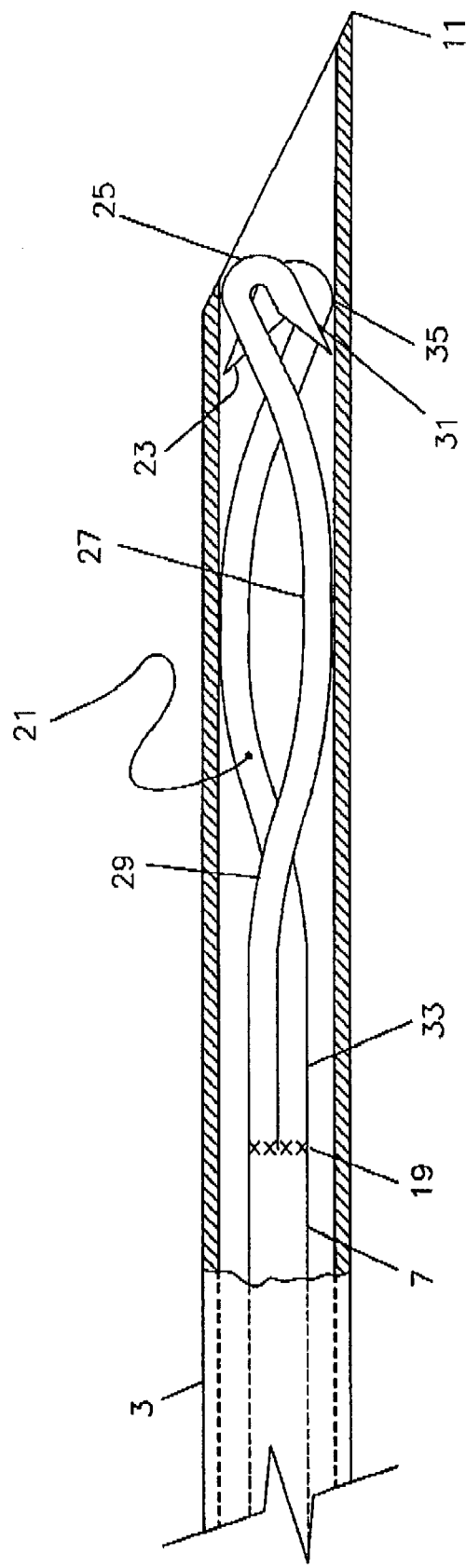
FIG. 2 is an enlarged plan view with partial section of the engaging element of FIG. 1 in an undeployed position within the needle. This view illustrates both a pre-deployment state and a retracted state.

In its undeployed state, the engaging element 9 is positioned longitudinally within the needle 3 lumen as shown in FIG. 1 and FIG. 2. The outer diameter of the plunger rod 7 and the weld section 19 are dimensioned such that they fit longitudinally within the lumen of the needle 3. The engaging element 9 includes at least one hook member such as a wire element 21 as shown in FIG. 2 although two wire elements 21 are preferred. Each wire element 21 includes a resilient proximal section and a hook. In the embodiment shown in FIG. 4, the resilient proximal section includes straight wire section 33, pre-bent wire sections 27 and 29, and the hook includes a pre-bent wire section 25, straight wire section 31 and an angled end section 23.

The various portions of the wire element 21 are configured to ensure that the angled end sections 23 can be advanced and retracted back into the needle 3 lumen without becoming ensnared on the wall of the needle at the needle tip 11 as will be explained in detail later herein. Each wire element 21 is comprised of a primary curve section 25, a secondary curve section 27, and a tertiary curve section 29. The wire elements 21 also include distal straight wire section 31 and proximal straight wire section 33. A sharp point is created by the angled end section 23.

Figure 4:
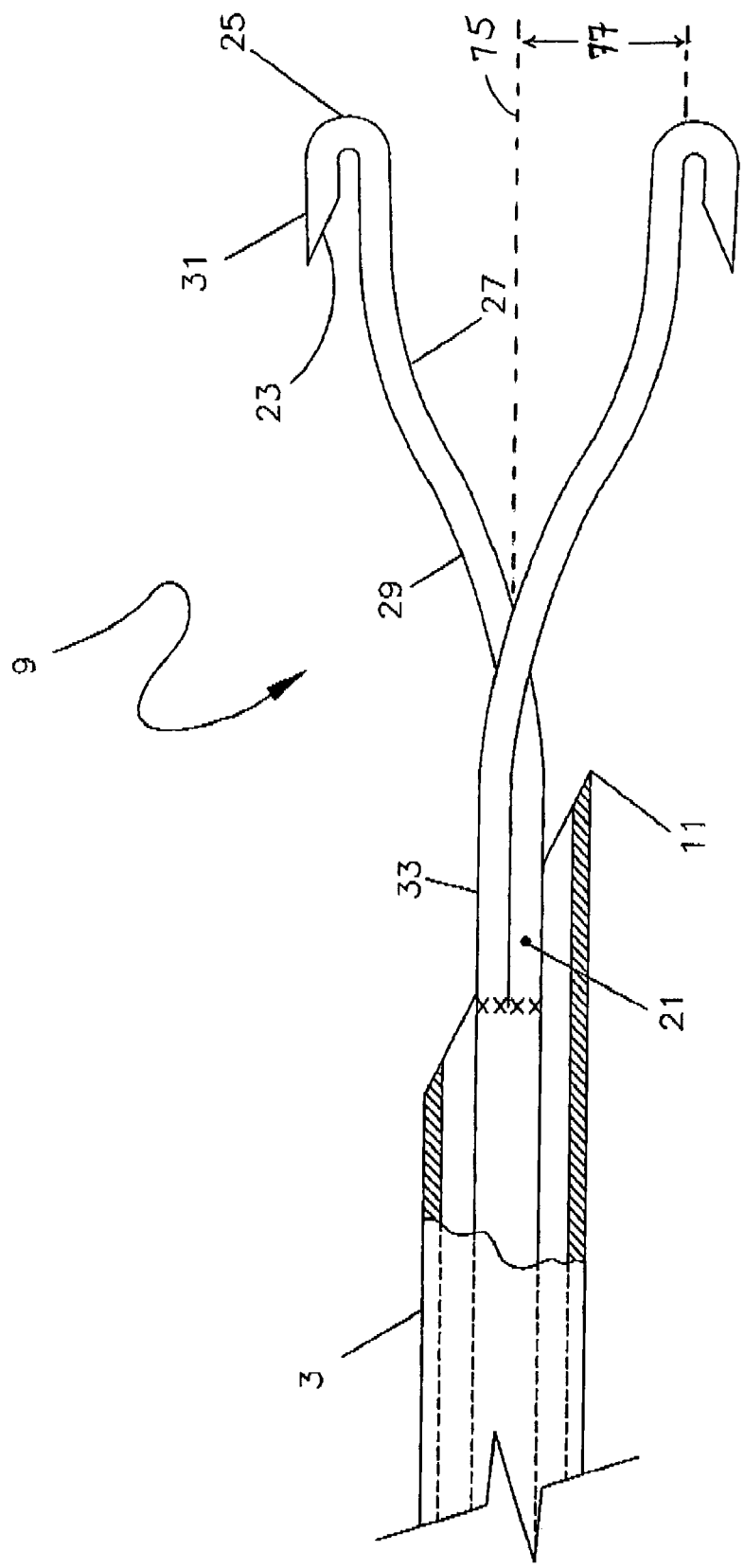
FIG. 4 is an enlarged plan view with partial section of the engaging element of FIG. 1 in a deployed position.

To fabricate the wire element 21, the distal ends are sharpened to a point 23 using techniques well known in the art. Other end point 23 geometries including multiple bevels, pencil point, and barbed configurations may also be used. The wire element 21 is then pre-bent into the configuration shown in FIG. 4. Preferably, the wire elements 21 are of spring-tempered stainless steel, although other shape memory materials such as Nitinol can be used. As shown in FIGS. 2 and 4, the wire 21 is pre-bent 180 degrees at bent wire section 25, aligning with the plane of the straight wire section 31.

When contained in an undeployed position within the lumen of the needle 3, the bent wire sections 27 and 29 are held in a substantially unbent position by the inner wall of the needle 3. The hooks 23, 25, 31 for the two wire elements 21 overlap each other as shown in FIG. 2. The bends 27 and 29 may be manufactured with a larger radius than depicted in FIG. 2 to minimize the amount of friction generated between the bent section 29 and the inner wall of the needle 3 when the engaging element 9 is being deployed or retracted. The position of the straight wire section 31 relative to the bend 27 is substantially parallel. This parallel position maximizes the needle 3 lumen space, providing space for multiple wire elements 21 while maintaining the small needle 3 outer diameter desired for small punctures. This alignment also provides space for blood flow needed to visually confirm correct positioning within the vein. The wire elements 21 may take on other configurations including single radius curve and straight shapes.

Figure 3:
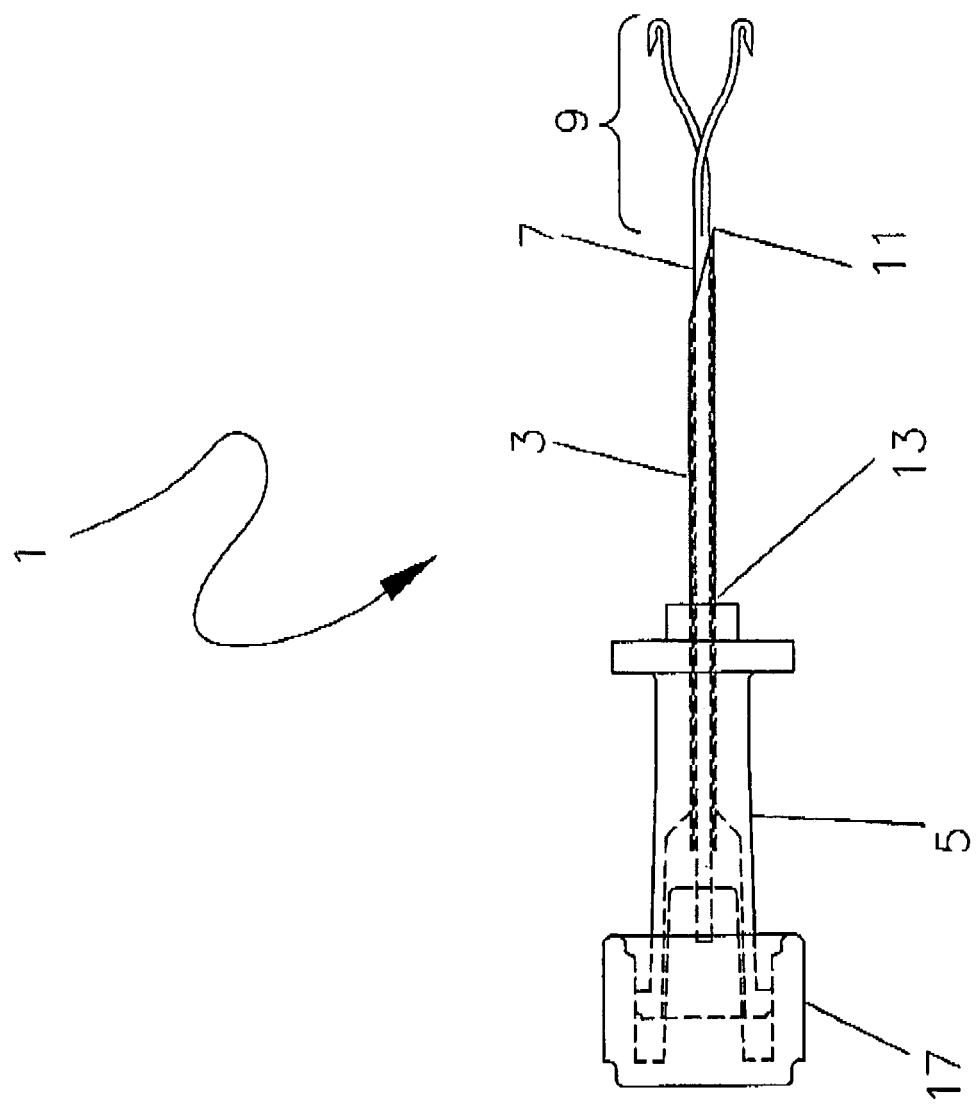
FIG. 3 is a plan view of the primary embodiment of the targeted phlebectomy device in a deployed position.

FIG. 3 shows the targeted phlebectomy device 1 after deployment of the engaging element 9. The engaging element 9 can be deployed by either pushing the end cap 17 toward the hub 5 causing the plunger rod 7 to advance or by retracting the needle hub 5 while holding the plunger rod 7 stationary. Either motion will cause the engaging element 9 to be deployed through the distal end of the needle 3 into the target vessel. Once outside the restriction of the needle 3 walls, the engaging element 9 will expand out into its pre-bent shape, as shown in FIG. 4. Specifically, the resilient proximal section comprising 27, 29, 33 extends outwardly in a radial direction with respect to the longitudinal axis 75 of the needle 3. Thus, the resilient proximal section has a substantial radial component 77. As can be seen in FIG. 4, the resilient proximal section and the hook for the two wire elements 21 extend radially outwardly in substantially different directions. Conversely, retraction of the engaging element 9 from the deployed state to the undeployed state causes the resilient proximal section 27, 29, 33 and the hook 23, 25, 31 to move radially inwardly to prevent the hook from engaging the wall of the needle tip 11 as will be explained in detail later herein.

In the deployed position, the end-cap 17 is optionally in contact with the proximal end of the needle hub 5. In the embodiment shown, the end-cap 17 is a standard Luer fitting which may be securely connected and locked to the hub 5 by rotating to engage the threads of needle hub 5. The device 1 can then be manipulated as a single unit which provides several advantages. For example, rotating the device when the engaging element 9 is fully deployed causes the engaged vessel wall to be wound around the engaging element 9, which increases the gripping force of device 1 on the vein. The user may grip the needle hub and rotate to disconnect the connecting tissue and to tease out the vein. The device 1 can then be withdrawn as single unit from the puncture opening.

A method of using the targeted phlebectomy device 1 will now be described with reference to FIGS. 5A-5F. FIG. 5A depicts the device 1 where the needle 3 is inserted into the vein 39 prior to deployment of the engaging element 9. At this point, the engaging element 9 is in an undeployed state and positioned within the lumen of the needle 3. FIG. 5B illustrates deployment of the engaging element 9 within the vein lumen 41. FIGS. 5C through 5F demonstrate the technique of engaging and withdrawing the diseased vein segment through the puncture site. The exposed vein segment can then be grasped with forceps and retracted.

The procedure begins with conventional pre-operative preparation of the patient as documented in published ambulatory phlebectomy literature. Prior to the surgical treatment, the patient's diseased venous segments may be marked. Marking may be guided by visualization, palpation, or if necessary, ultrasound. Often, the diseased vein segments may be sufficiently visible to allow direct penetration by the phlebectomy device 1 without marking. Local anesthetic is typically administered along the vein segments to be extracted before the procedure is started.

To access the diseased vein segment, the beveled tip 11 of the needle 3 is inserted into the skin 37 and advanced until the needle penetrates into the lumen 41 of the varicose vein 39, as shown in FIG. 5A. At this stage, the engaging element 9 is in the undeployed state inside the needle 3. During the skin puncture step, the patient is in a supine or semi-upright position if necessary. With the patient in semi-upright position, the target veins remain more visible and are easily palpable since they are not emptied of blood. This position allows for easy visualization and precise targeting of the diseased vessel.

The current invention can also be used to eliminate incompetent or varicose veins that are not visible or palpable, thus overcoming the disadvantages of the traditional stab avulsion technique. Ultrasonic imaging is used to locate the underlying deep diseased or refluxing vein. Once located, the targeted phlebectomy device 1 is inserted into the target vein 39 under ultrasound guidance. Large incisions, and the resulting scarring typically associated with stab avulsion are thus eliminated with the current invention. Veins located as deep as 5 cm under the skin surface can be removed using the device. The maximum access depth is limited only by the length of the needle 3 cannula and the elongation characteristics of the target vessel. Accordingly, the current invention can be used to not only extract veins of varying diameter but also of varying depth beneath the skin surface without requiring multiple devices and extraction techniques.

Correct positioning of the needle 3 within the vein lumen is confirmed by visualization of blood in the hub 5 lumen. Visual confirmation of correct position prior to extraction is a significant procedural advantage over traditional phlebectomy hooks, forceps and scalpels. With the present invention, the presence of blood within hub 3 indicates that the device 1 has correctly targeted a vein and is positioned as shown in FIG. 5B before retraction occurs. Advantageously, the chance of inadvertently hooking and avulsing a nerve or other non-targeted structure is greatly reduced when using the present invention because visual confirmation of positioning is easily achieved.

The device 1 will capture and retain the blood within the lumen of the needle hub 5 because of the relatively vertical position of the device 1 during treatment. Since the vessel being punctured is a low-pressure vein, the flow rate and volume of blood entering the needle hub 5 lumen from the vein is sufficient to confirm correct positioning but is insufficient to fill and overflow from the proximal opening 15 of the needle hub 5.

Once correct positioning of the needle 3 within the vein lumen 41 has been established, the end cap 17 is depressed or pushed forward. Alternatively, the needle 3 can be withdrawn away from the vein while the plunger rod 7 or end cap 17 is held stationary. Either of these actions will deploy the engaging element 9 within the vein lumen 41. FIG. 5B depicts the targeted phlebectomy device 1 after deployment within the vein lumen 41. When the end cap 17 is fully seated against the proximal opening of the hub 5, the engaging element 9 will have advanced down the needle 3, through the needle tip 11 and be positioned completely outside of the needle as shown in FIG. 5B.

It is desirable to provide the least amount of friction possible when the plunger rod 7 as deployment device for the engaging element is being pushed in order to assist the physician in feeling the engaging element 9 being deployed inside the target vein. Friction may cause difficulty in advancing and positioning the engaging element 9. The open design of the hub 5 creates a relatively friction-free pathway for the longitudinal advancement of the plunger rod 7. The absence of a sealing mechanism within the hub lumen substantially eliminates friction, allowing the user to confirm correct positioning tactilely. Another advantage of the open hub design is that the device is less expensive and less time-consuming to manufacture due to elimination of a sealing element.

To extract the vein segment 39 through the puncture site, the device 1 is withdrawn away from the skin surface 37. As the needle 3 is withdrawn, the pointed end sections 23 of the engaging element 9 are pulled into and become embedded into the inner wall of the varicose vein nearest to the puncture site, as depicted in FIG. 5C. At this point, the pointed end sections 23 of the engaging element 9 are fully engaged with the inner vein wall. The straight wire segment 31 (FIG. 2) is dimensioned such that the pointed end section 23 will embed into the vein wall without protruding through the wall and into the surrounding tissue. Typically, the straight wire segment 31 ranges from 0.5 to 2.0 mm. As shown, the segment 31 is about 1.25 mm in length. As the needle 3 is gradually withdrawn from the puncture site, as shown in FIGS. 5D-5F, vein wall 39 is pulled upward through the puncture site by the tensile force applied by the device to the vein wall 39.

To enhance the gripping force of the engaging elements 9 on the vein or other tubular structure, the end cap 17 may be rotated. This action causes the plunger rod and the deployed engaging elements to rotate. As the engaging elements 9 rotate, the vessel segment becomes wound around the engaging element thus increasing the overall gripping force of the device on the vein. In addition to increasing the gripping force, this rotating action also provides protection to the puncture track during withdrawal of the device. Specifically, the segment of the vessel 39 that is wrapped around the engaging element 9 provides a protective barrier between the pointed ends 23 of the elements 9 and the puncture track wall which reduces the risk of trauma to the puncture track during withdrawal.

During withdrawal, the needle puncture site will dilate slightly to allow the passage of the vein segment and the engaging element 9. As tensile force is applied to the vein segment being withdrawn, it will stretch and the walls become elongated and thinner, thus facilitating passage of the segment through the puncture track without significant expansion or tearing of the track. Tensile force will also cause the engaging element 9 to straighten at bend sections 27 and 29 (FIG. 2) and bring the wire elements 21 together to the extent that the engaging elements fit through the puncture path without causing tearing of the tissue, as shown in FIG. 5D through FIG. 5F.

The device can be used to apply gentle traction to the vein to free it from fibrous attachments and perforators. Having a unitary device 1 in which the components are secureably connected by the end cap 17 enhances the torquability and traction that can be applied to the vein segment. Once the vein has been exteriorized from the skin 37 surface (FIG. 5F), it can be grasped with forceps and further removed. The exposed vein is then teased out and cut.

The free end of the vein segment can be pulled through the additional puncture sites using techniques well known in the art to expose and withdraw the vein segment. The entire length of the diseased vein segment is treated in this manner. A new phlebectomy device 1 may be used for each puncture. Alternatively, the device 1 can be disengaged from the removed vein segment and reloaded by retracting the engaging elements 9 within the needle. Reloading of the targeted phlebectomy device 1 allows the user to retract the engaging element 9 back into the needle 3 lumen without engaging the vein or other tubular bodily structure.

The shape configuration of the engaging element 9 depicted in FIG. 3 and FIG. 4 allows the engaging element 9 to be withdrawn into the needle without actually engaging and retracting the vein or other bodily structure. This retractability feature can be advantageous in the event that the engaging element 9 is mistakenly deployed into untargeted tissue or other bodily structure. For example, the user may inadvertently deploy the engaging element 9 outside of the targeted vein. Rather than withdrawing the device with engaging element 9 exposed in a deployed position, which will cause unnecessary trauma, the user can retract the engaging element 9 into the needle 3 lumen. The device 1 can then be withdrawn from the puncture site, repositioned and redeployed at a new location.

To retract the device 1 without engaging and extracting the vein or other bodily structure, the plunger rod 7 is pulled back while the needle 3 is held stationary or advanced slightly within the puncture track. This action will cause the engaging element 9 to be repositioned within the lumen of the needle 3, as illustrated in FIG. 2. After retracting the engaging element 9 back within the needle 3 lumen, the device 1 can be removed from the insertion site, re-positioned and then redeployed through a new insertion site.

Referring to the engaging element 9 configuration of FIG. 2, the shape of each wire element 21 includes pre-formed bend sections and straight sections that are dimensioned and curved so as to ensure that the angled end sections 23 can be retracted back into the needle 3 lumen without becoming ensnared on the wall of the needle at the needle tip 11.

During retraction of the engaging element 9 for re-positioning purposes as described above, contact of the secondary curve section 27 with the inner wall of the needle 3 forces a portion of the primary curve section 25 to be pushed against the inner wall of the needle 3. FIG. 2 illustrates the position of wire elements 21 after it has been retracted back into the needle 3 lumen. The primary curve section 25 is in contact with the inner wall of the needle 3 at point 35. The location of the contact point 35 ensures that the angled end sections 23 can be retracted fully within the needle 3 lumen without becoming ensnared on the needle tip 11.

The length of the distal straight wire section 31 and span of the primary curve section 25 are dimensioned such that the engaging element 9 will retract smoothly into the needle 3 lumen. The span of the primary curve section 25 is sized to be less than the needle 3 inner diameter. Thus, the combined design of the primary curve 25, the distal straight section 31 and the radius of the secondary curve section 27 produce an engaging element that will retract without the angled distal ends 23 becoming ensnared upon the wall of the needle tip 11 during the retraction process.

Figure 6:
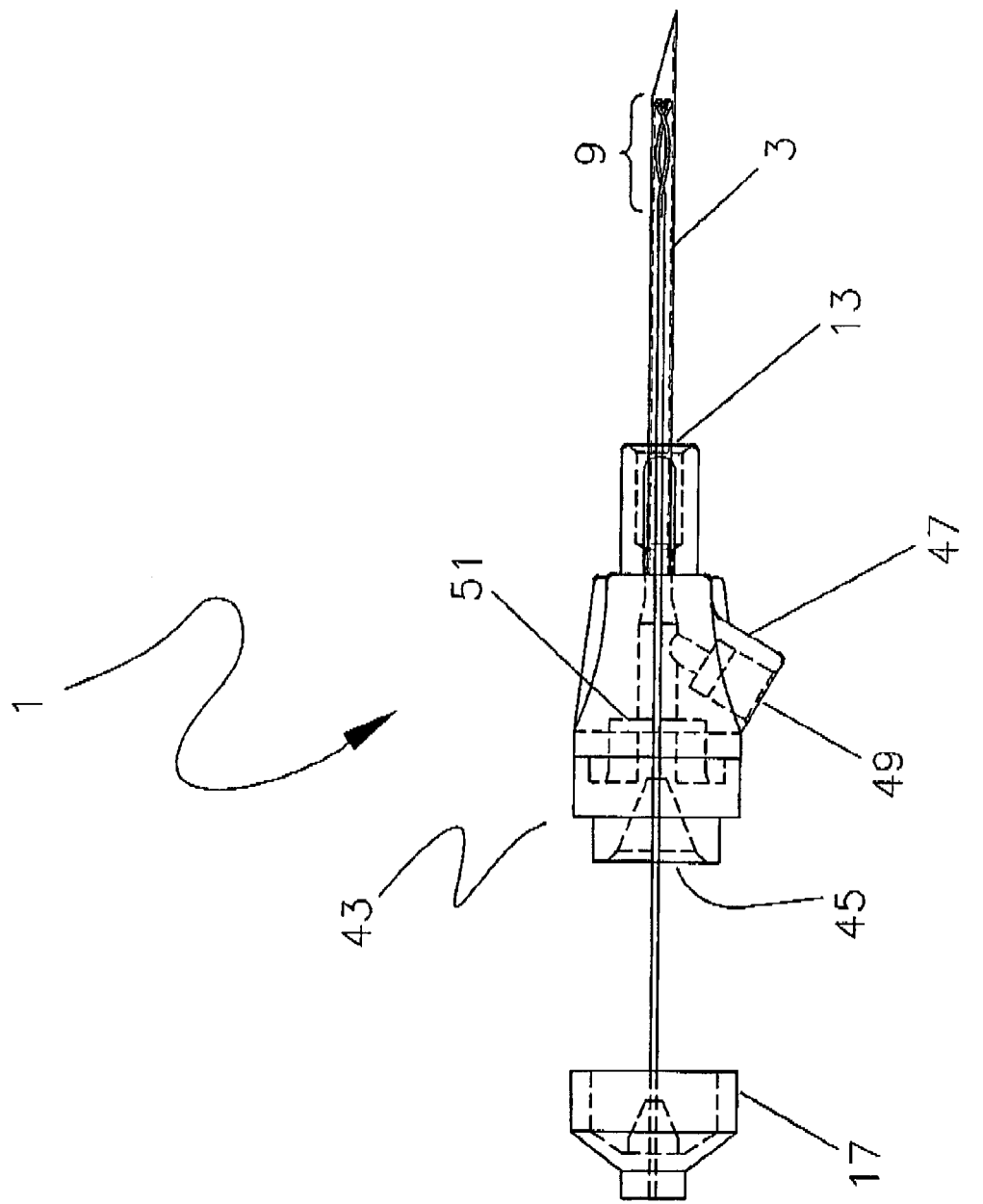
FIG. 6 is an alternative embodiment of the targeted phlebectomy device in an undeployed position and featuring a bloodless hub configuration.
Figure 7:
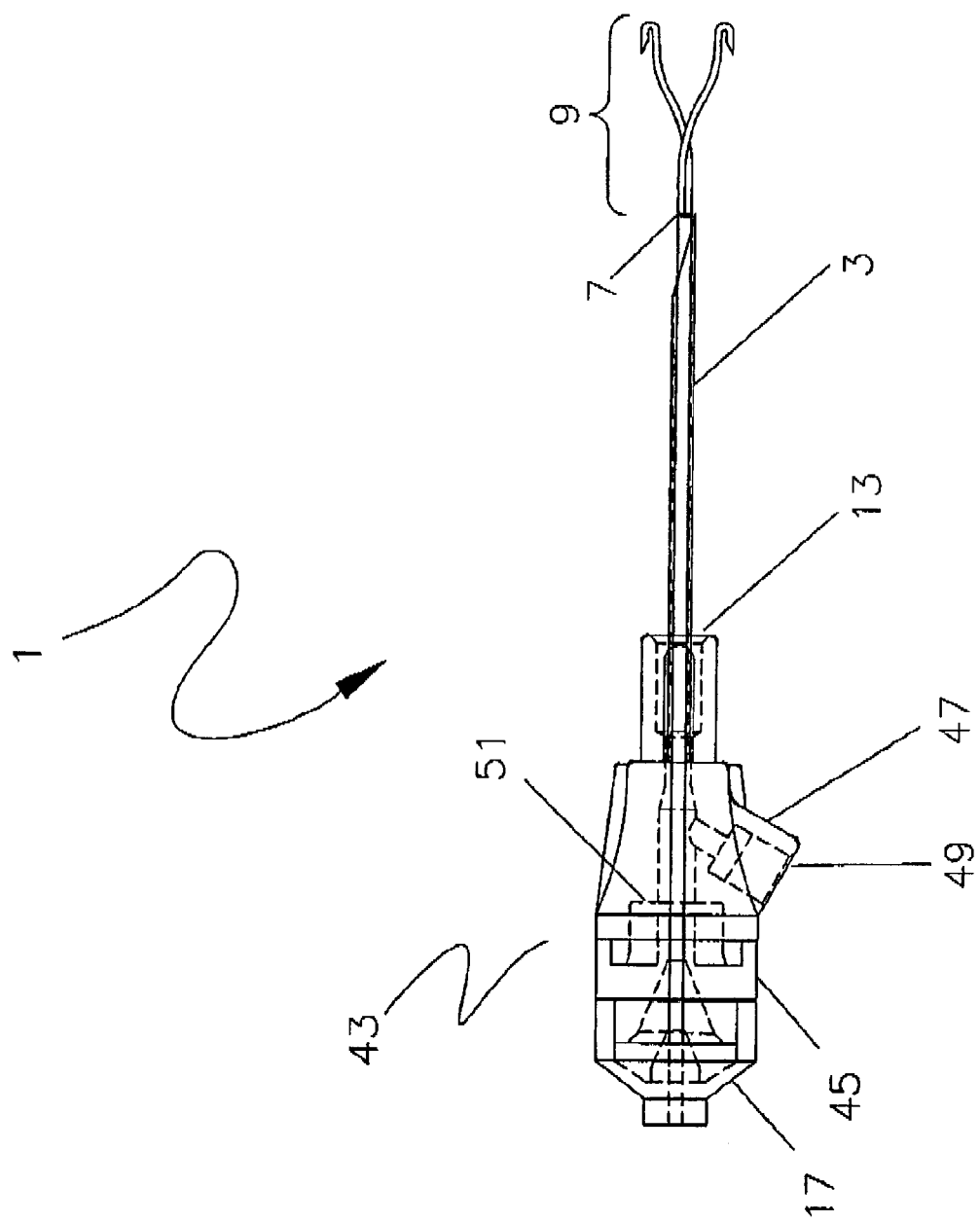
FIG. 7 is a plan view of the targeted phlebectomy device of FIG. 6 in a deployed position.

Turning now to alternative embodiments of the targeted phlebectomy device, a bloodless hub configuration is depicted in FIG. 6 and FIG. 7. The hub 43 is constructed of a clear or other plastic material commonly used in the medical device industry so as to allow visual confirmation of blood flow indicating correct placement within the vein. As shown in FIG. 6, the hub 43 includes a through lumen port 45 and a side port 47. The needle 3 extends beyond the through lumen distal hub opening 13 by approximately 1 to 5 cm. A standard adhesive is used to attach the needle component 3 to the through lumen opening 13.

The device allows air to escape and blood to enter without blood exiting the fitting. To accomplish this, a porous plug 49 or other closure element is used to close off the side port 47 opening. Similarly, a sealing gasket 51 constructed of silicone or other type of sealing material is located within the lumen of the through lumen port 45. The sealing gasket 51 provides a leak-proof barrier to prevent the backflow of blood through the port while still allowing forward movement of the plunger rod 7. Thus, the design of the hub 43 ensures that the captured blood does not escape through either the through lumen port 45 or the side port 47.

As shown in FIG. 7, the engaging element 9 is designed as previously described in the first embodiment of FIGS. 1-4. When pressure is applied to the end cap 17, the plunger rod 7 advances forward through the lumen of hub 43. The forward movement causes the distal end of the plunger rod 7 to advance the engaging element 9 through the needle 3 lumen and into the target tubular structure. When the end cap 17 is fully seated against the proximal end of the through lumen port 45, the engaging element 9 will be positioned completely outside of the needle 3 as shown in FIG. 7.

Figure 8:
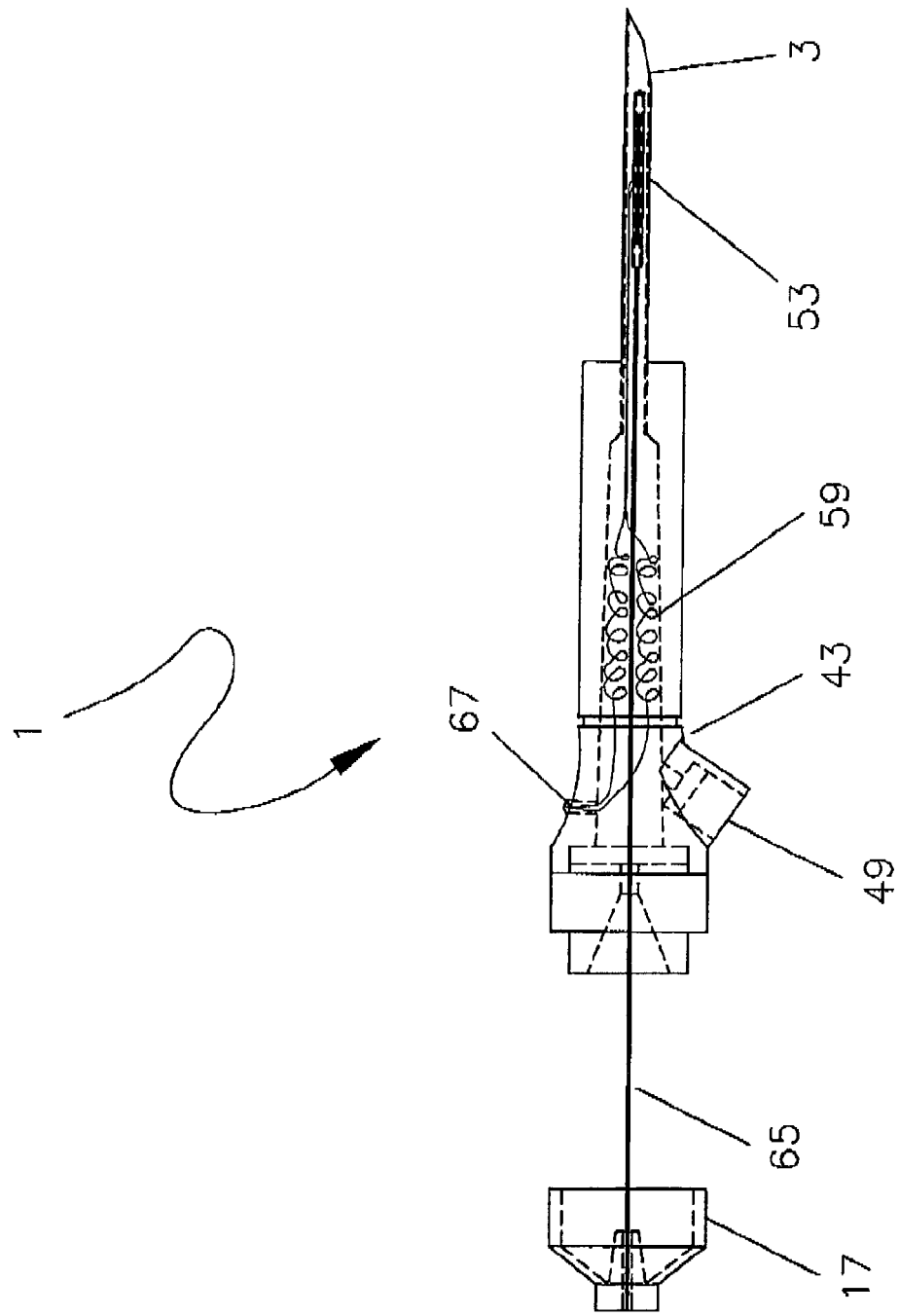
FIG. 8 is a plan view of another embodiment of the targeted phlebectomy device in an undeployed position. This embodiment uses a T-Bar structure to engage the vein.
Figure 9:
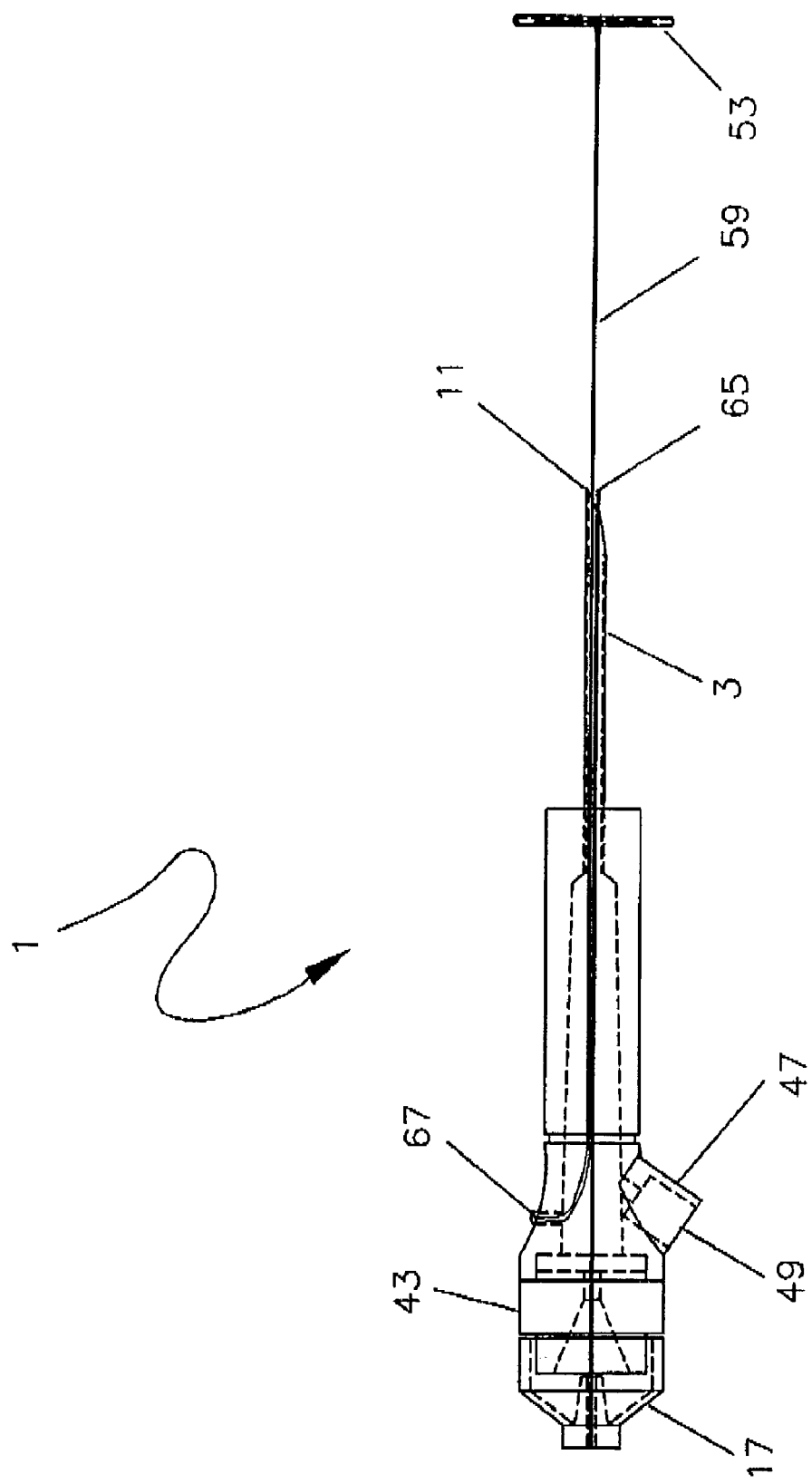
FIG. 9 is a plan view of the targeted phlebectomy device of FIG. 8 in a deployed position.

Turning now to alternative embodiments of the engaging element, FIG. 8 depicts a targeted phlebectomy device with a T-bar configuration of the engaging element. The T-Bar component 53 is comprised of an outer plastic casing 55, spring wire element 57, and a length of cord such as a suture line 59 (see FIG. 10). In its undeployed state, the T-bar component 53 is positioned within and parallel to the needle 3 lumen, as shown in FIG. 8.

A length of double suture line 59 is stowed within the lumen of the hub 43 in a coiled fashion. Typically, between 5 to 10 cm of slack suture length will be stowed within the hub 43 lumen of the targeted phlebectomy device 1 when in the undeployed position. The slack in the suture line 59 is taken up as the T-bar component 53 moves from the undeployed to the deployed position.

The pusher rod 65 of the targeted phlebectomy device is the mechanism by which the T-bar component 53 is deployed within the vein. The pusher rod 65 is made of semi-flexible solid material and is attached at the proximal end to the plunger end cap 17. The pusher rod 65 is not directly attached to the T-Bar component 53. Instead, the distal end of the pusher rod 65 is in contact with but separate from the proximal end of the T-Bar component 53. When the pusher rod 65 is advanced, the distal end of the rod comes in contact with and forces the T-Bar component 53 to advance forward through the needle 3 cannula The suture wire 59 is permanently attached to the hub body 43 at location 67 and to the T-Bar component 53. As the T-bar component 53 is advanced forward into the vein by the plunger rod 7, the coiled section of the suture wire 59 unwinds to provide sufficient slack for the T-bar component 53 to enter the vein without being under tension from the suture wire. At this stage, the engaging element (T-bar component) 53 is in the deployed state. In the fully deployed state, the distal end of the pusher rod 65 extends past the needle tip 11 by approximately 1-5 mm. This deployed position is desirable to ensure complete clearance of the T-bar component 53 past the needle tip 11.

Figure 10:
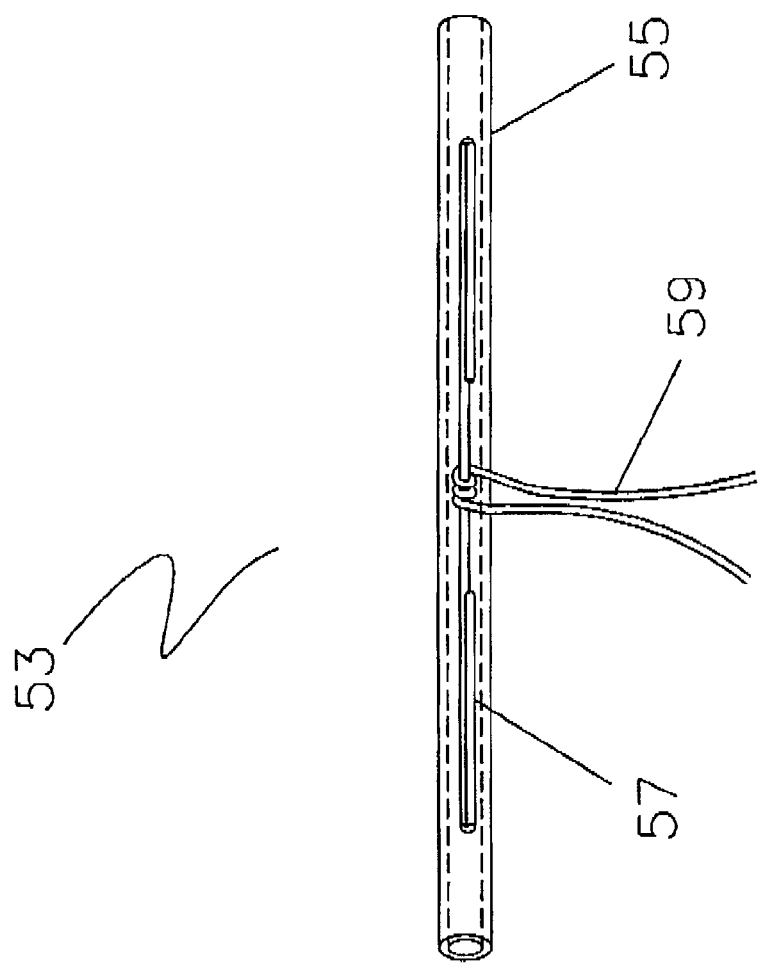
FIG. 10 is an enlarged plan view of the T-Bar element shown in FIGS. 8 and 9.

A detailed view of the T-Bar component 53 is illustrated in FIG. 10. The T-Bar component 53 is comprised of at least one spring wire element 57 with a plastic casing 55. The plastic casing 55 is a tubular structure with open ends whose outer diameter is slightly smaller than the inner diameter of the needle 3. The plastic casting 55 can also be a jacket structure molded over the spring wire element 57. In one embodiment, the inner diameter of the needle is about 0.039 inches. Preferably, the plastic casing 55 is 6 to 10 mm in length with an outer diameter of between 0.025 to 0.028 inches. Centered within the lumen of the T-bar plastic casing 55 is a spring wire element 57. The spring wire 57 is of such a length so that it provides added support to the center section of the plastic casing 55. Typically, the spring wire 57 element is positioned within the center portion of the plastic casing 55 and is approximately 5-10 mm in length.

The T-bar component 53 is constructed of flexible material and profiled such that it will bend slightly under force of withdrawal. During deployment into the vein, the T-Bar component is advanced through the needle 3 cannula into the vein. As force is applied to the device 1, the T-Bar component becomes perpendicular to the needle 3 and aligned along the longitudinal axis of the vein. Further traction on the needle 3 causes the T-bar component 53 to be positioned against and engages the vein wall. As additional traction is placed on the needle 3, the T-Bar component 53 will bend from its midpoint into an arc. During withdrawal, the needle puncture site will dilate slightly to allow the passage of the vein and bent T-bar component 53. The T-bar component 53 will bend to the extent that it is able to fit through the puncture path without causing tearing of the tissue.

The suture line 59 is attached to the spring wire element 57 at its center. In one embodiment, the diameter of each suture 59 is about 0.0075 inches. The suture line 59 may be attached to the wire element 57 by a wrapping process, a knot or through a chemical bonding process. The suture line 59 is attached to the mid-section of the spring wire 57 such that two end portions of the suture line extend away from the wire element 57. These end portions extend through the need 3 lumen, into the lumen of the through lumen port 47, and through a small side opening at point 67 in the hub 43. The suture lines 59 are secureably attached to the hub 43 at suture attachment point 67 in FIG. 8. The means of attachment may be an oversized knot or an adhesive or combination thereof.

Figure 12:
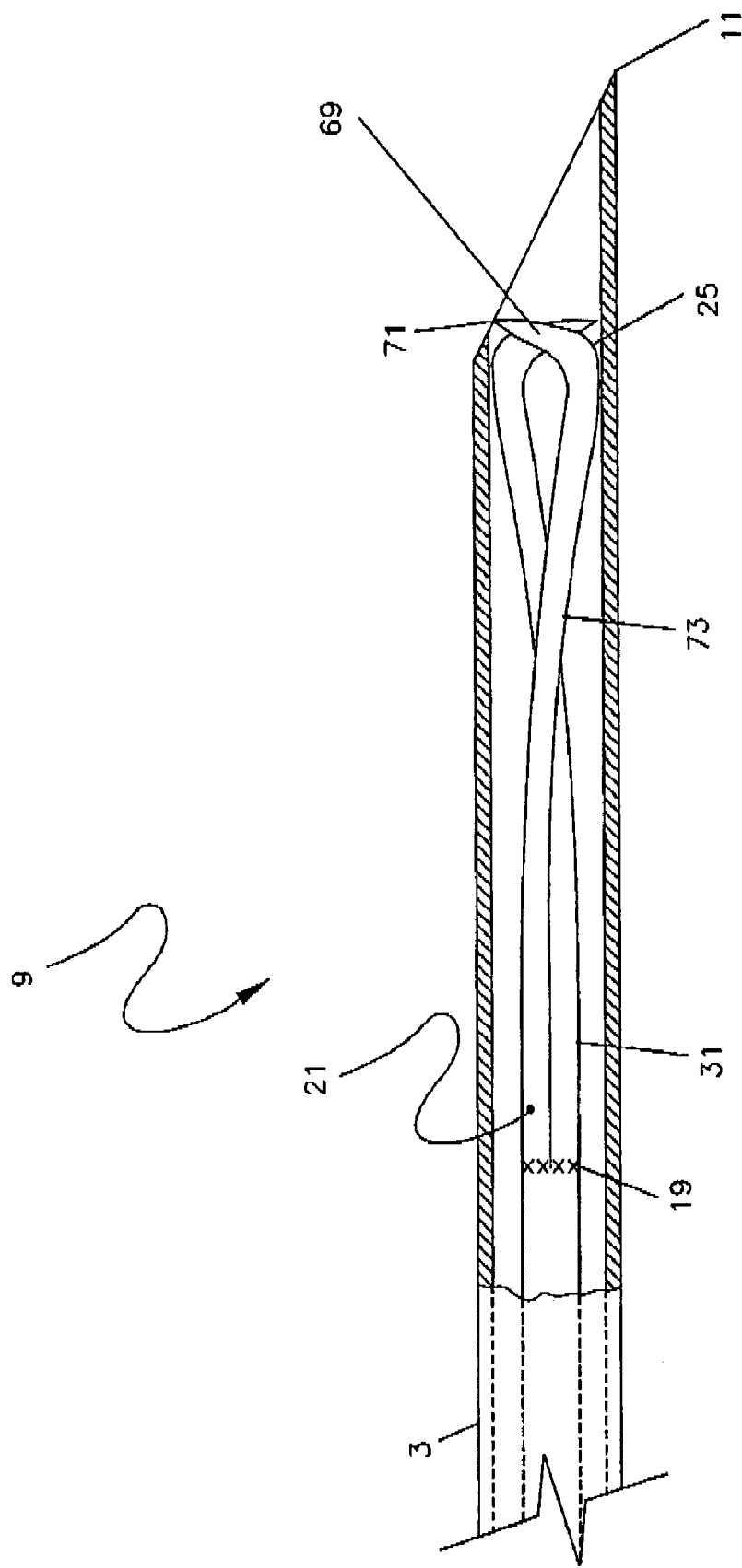
FIG. 12 is an enlarged plan view with a partial section of an alternative embodiment of an engaging element in an undeployed position.
Figure 13:
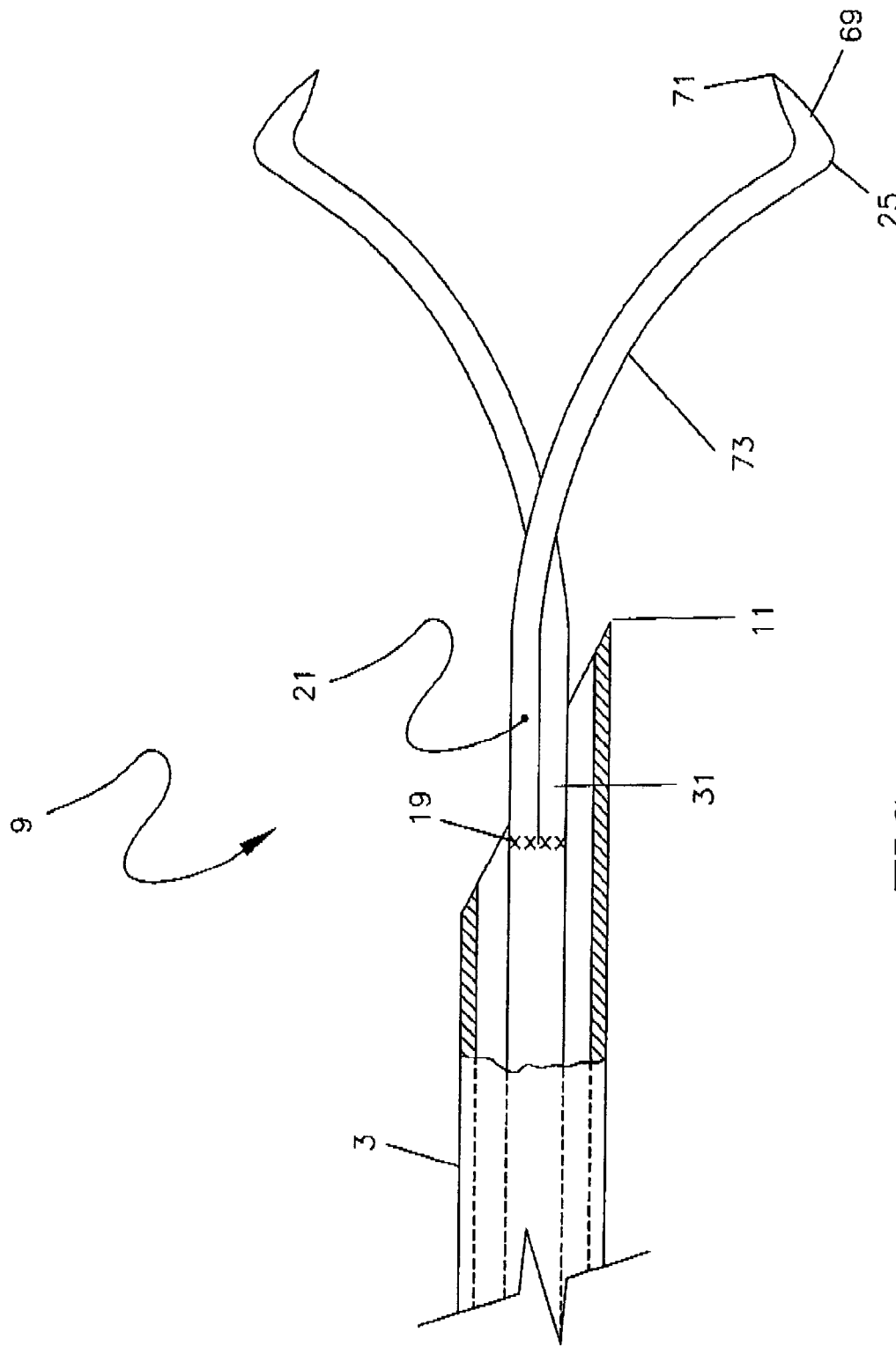
FIG. 13 is an enlarged plan view with a partial section of an alternative embodiment of an engaging element in a deployed position.

Another embodiment of the engaging element is depicted in FIG. 12 through FIG. 14. The engaging element of this embodiment is similar to the embodiment depicted in FIG. 2 and FIG. 4 with the exception of the orientation of the distal end section. Referring to the engaging element 9 configuration of FIG. 12, the shape of each wire element 21 is comprised of the weld section 19, straight wire section 31, secondary curved section 73, a primary curve section 25, distal end section 69 and a distal wire point section 71. In the embodiment of FIGS. 12-14, a resilient proximal section includes the straight wire section 31 and the secondary curved section 73 while a hook includes the primary curve section 25, distal end section 69 and a distal wire point section 71.

Unlike the FIG. 2 embodiment, this embodiment is designed to engage the posterior vein wall section opposite from the puncture hole. When the plunger rod 7 (not shown) is depressed to deploy the engaging element 9, the resilient proximal sections of the wire elements 21 expand radially outward into the deployed configuration shown in FIG. 13. The distal end points 71 are angled inward toward the axis of the needle and distally relative to the overall wire element 21 when fully deployed.

Figure 14A:
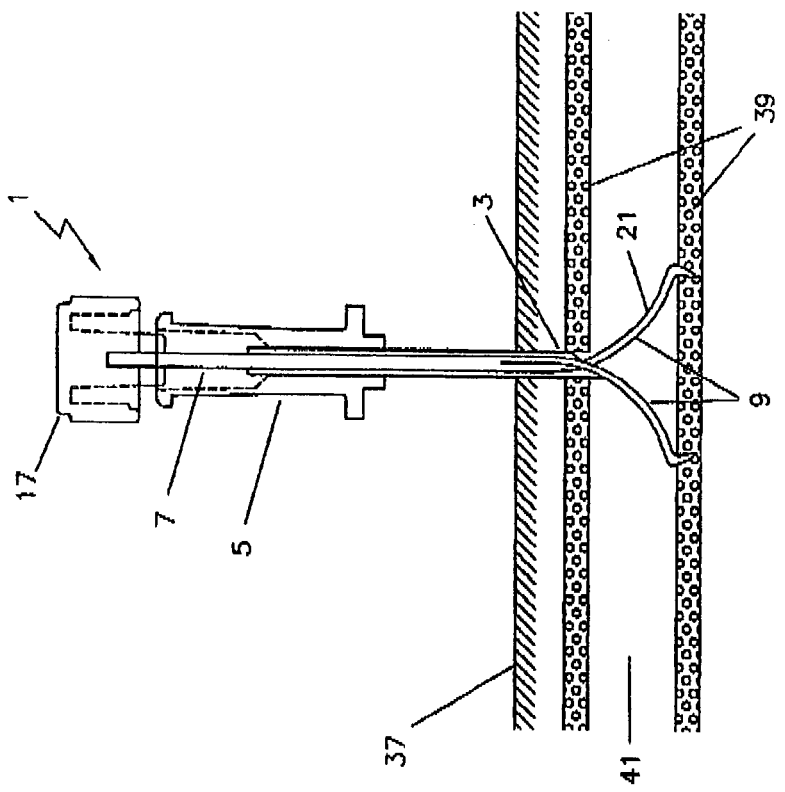
FIGS. 14A-14B depict a method of deployment and engagement of the engaging element of FIG. 12.
Figure 14B:
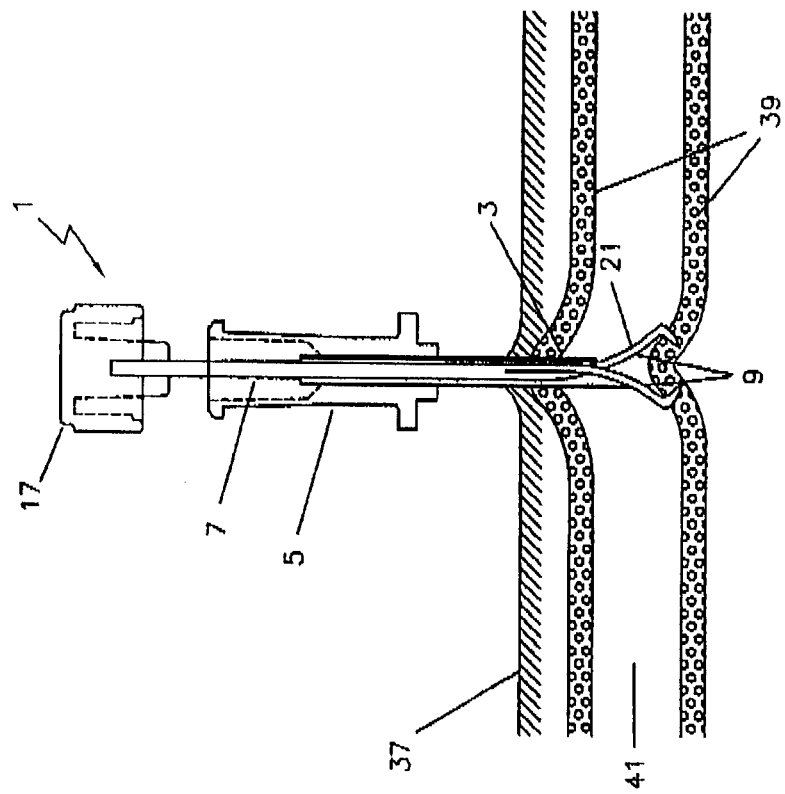

To deploy the engaging elements 9 and engage the vein, the vessel is first punctured with the needle 3. After verification of correct positioning, the plunger rod 7 is depressed to advance the engaging element 9 into the vein against the posterior vein wall 39 as shown in FIG. 14A. The needle 3 is then advanced forward slightly relative to the plunger rod 7. This movement causes the wire elements 21 to draw together thereby piercing and gripping the vein wall 39 to engage the vein as illustrated in FIG. 14B. The plunger rod 7 may be optionally retracted to further enhance the gripping force of the wire elements 21 on the vein wall 39. The vein is then extracted through the puncture track as previously described.

The orientation of the distal end sections 69 and end point 71 are shaped such that the engaging element 9 can be easily advanced and retracted back into the needle 3 lumen without becoming ensnared on the wall of the needle at the needle tip 11. This feature allows the user to reposition and redeploy the device as needed. To reposition the device 1 without extracting the vein, the user retracts the engaging elements 9 without advancing the needle 3. This movement causes the non-sharp portions of the engaging elements 9 to be positioned against the anterior vessel wall 39. The end points 71 will not engage the anterior vessel wall because the orientation of distal end sections 69 is away from the vessel wall.

Figure 11:
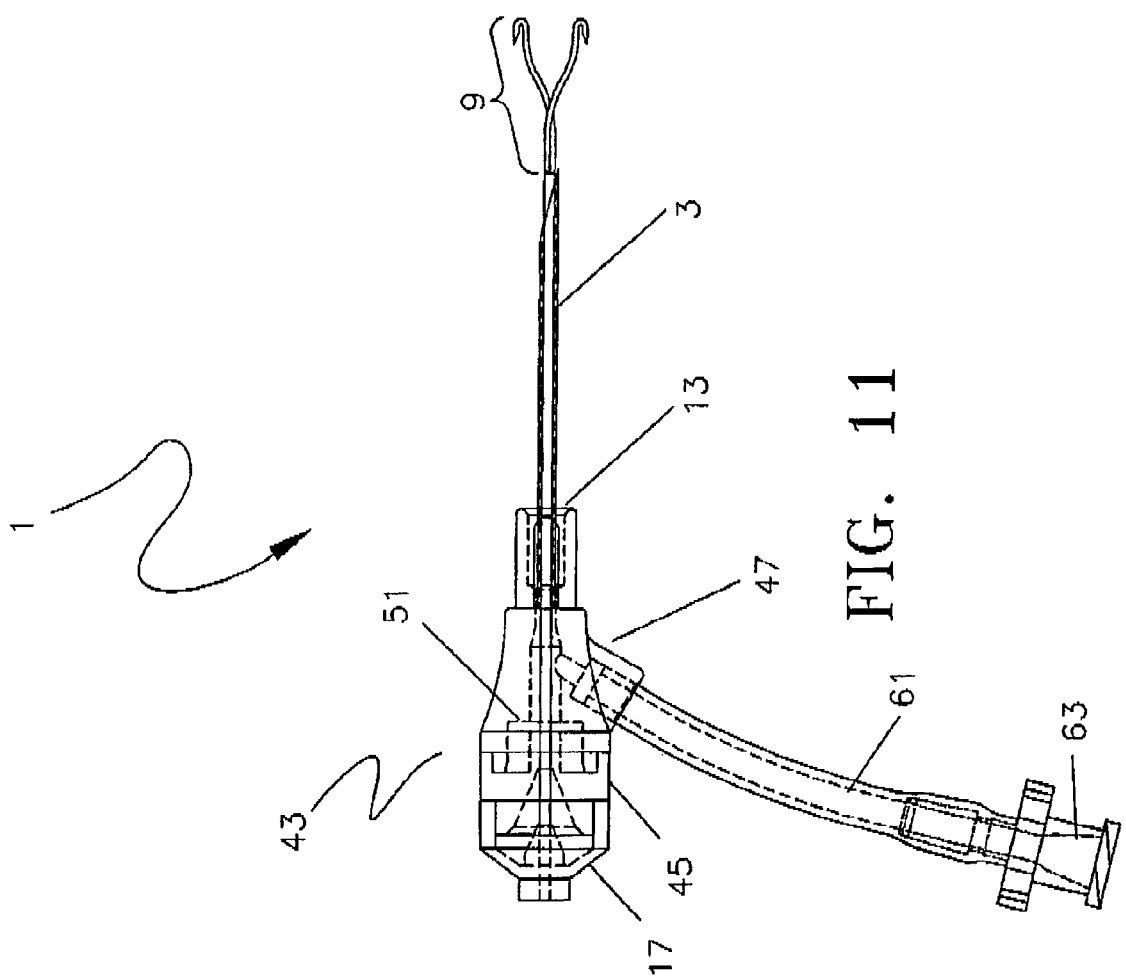
FIG. 11 is a plan view of an alternative embodiment of the targeted phlebectomy device with ability to inject fluid through the needle.

FIG. 11 depicts a targeted phlebectomy device with side port extension tubing and fitting that can be used to inject saline and other fluids into the tubular structure during the procedure. The targeted phlebectomy device 1 of this embodiment includes flexible side port extension tubing 61. A standard syringe or other injection device may be connected to the side port extension tubing 61 at the barred luer fitting 63. Fluid injected through the syringe will travel through the lumen of side port extension tubing 61 and into the lumen of the hub 43, exiting through the distal end of the needle 3 into the target tissue.

The infusion of saline or other fluid can be used as a tumescent agent to temporarily increase the size of the targeted vessel for more accurate positioning. It may also be desirable to inject anesthetic agents directly into the lumen of the tubular structure for pain reduction. The device of this embodiment can also be used for a combined phlebectomy/sclerosing procedure by injecting a sclerosing agent through the side port into the vein. The side port can also be used to apply a slight vacuum to the needle to aid in the visualization of blood flashback indicating correct needle tip placement within the vein.

A novel targeted phlebectomy device has been described above. The invention uses a single device to perform the function of accessing the vein and the function of extracting the vein through a single puncture in a precisely targeted manner. As a result, the physician is not required to switch out the needle component with a separate phlebectomy hook or other similar extraction device. Also, because the present invention uses an engaging element that can be positioned inside the vein without using any external hooking device, the time-consuming and inaccurate process of hooking the vein segment is avoided. In particular, twisting, rotating, and otherwise maneuvering a hooking instrument to locate and grasp the vein segment is not required with this invention. Instead, a precisely targeted extraction device locates the vein, provides visual confirmation of correct position and retrieves the vein to pull it through the puncture site with only a slight dilation of the entry site. Thus, tearing, stretching and over-dilation of the puncture site is minimized using the present targeted phlebectomy device 1.

The current invention can be used to eliminate incompetent or varicose veins that are not visible or palpable, thus overcoming the disadvantages of the traditional stab avulsion technique. Ultrasonic imaging may be used to locate the underlying deep diseased or refluxing vein. Once located, the targeted phlebectomy device is inserted into the target vein, the vein is engaged and extracted through the small needle puncture track. Large incisions, and the resulting scarring, are thus eliminated with the current invention. Veins located as deep as 5 cm under the skin surface can be removed using the device. The maximum access depth is limited only by the length of the needle cannula and the elongation characteristics of the target vein. Accordingly, the current invention can be used to not only extract veins of varying diameter but also of varying depth beneath the skin surface without requiring multiple devices and extraction techniques.

Various other embodiments of the invention are possible. The size and shape of the hub component can be modified to accommodate various needle sizes, gripping contours and deployment mechanisms. The hub may include winged flange or other configuration to facilitate ease of handling during the phlebectomy procedure.

The engaging component can take on several different forms as well. The length, material, design and contour of the engaging element can be modified to accommodate differing venous anatomy and deployment means so long as the engaging element is deployable through a needle and engages the vein. The engaging element can be provided as a stand alone component in a separate packaging to be assembled by the user prior to or during the procedure using a needle of choice.

Although the method of use is focused on the treatment of diseased veins, the use of this device for the extraction of other tubular structures within the human body is within the scope of this invention. Any bodily tubular structure may be targeted using this device.

While certain novel features of this invention have been shown and described above, the present invention may be embodied in other specific forms without departing from the spirit or essential characteristics of the invention. The described embodiments are to be considered in all respects only as illustrative and not as restrictive. Various omissions, modifications, substitutions and changes in the forms and details of the device illustrated and in its operation can be made by those skilled in the art without departing in any way from the spirit of the present invention.

What is claimed is:

1. A method of withdrawing a tubular body part under a skin using a device including a needle having an inflexible needle tip and an inflexible cannula extending from a proximal hub of the device and terminating at the needle tip, the needle being inflexible throughout its length relative to the longitudinal needle axis, the method comprising:
   puncturing the skin with the needle, the needle containing an undeployed engaging element;
   pushing the undeployed engaging element out of the inserted needle for deployment within and engagement with an inner wall of a tubular body part to be withdrawn; and
   pulling the needle and the deployed engaging element so as to withdraw through the punctured skin the tubular body part engaged by the engaging element.

2. The method according to claim 1, prior to the step of pulling, further comprising rotating a deployment device that is slidably coupled with the needle and is attached to the engaging element so as to rotate the engaging element.

3. The method according to claim 2, wherein the engaging element includes at least one hook, and the method further comprises, prior to the step of rotating, pulling the hook to engage the tubular body part.

4. The method according to claim 1, wherein the engaging element includes at least one hook, and the method further comprises, pushing the needle with respect to the deployed engaging element so as to engage a posterior wall of the tubular body part with the hook.

5. The method according to claim 1, prior to the step of pulling, further comprising retracting the deployed engaging element into the lumen of the needle without engaging the tubular body part.

6. The method according to claim 5, after the step of retracting, further comprising removing the inserted needle containing the retracted engaging element for reinsertion at a different site.

7. A method of removing a vein comprising:
   puncturing a skin and a vein underneath the skin with a needle, the needle containing an undeployed vein engaging element;
   pushing the undeployed vein engaging element out of the needle and through the punctured vein to deploy the vein engaging element inside the vein; and
   pulling the needle and the deployed vein engaging element so as to withdraw through the punctured skin the vein engaged by the engaging element.

8. The method according to claim 7, prior to the step of pulling, further comprising rotating a deployment device that is slidably coupled with the needle and is attached to the vein engaging element so as to rotate the vein engaging element.

9. The method according to claim 8, wherein the vein engaging element includes at least one hook, and the method further comprises, prior to the step of rotating, pulling the hook to engage the tubular body part.

10. The method according to claim 7, wherein the vein engaging element includes at least one hook, and the method further comprises, pushing the needle with respect to the deployed vein engaging element so as to engage the tubular body part with the hook.

* * * * *